United States Patent
Assouline et al.

(10) Patent No.: US 11,969,483 B2
(45) Date of Patent: Apr. 30, 2024

(54) POROUS NANOCARRIERS FOR THE MONITORING AND TREATMENT OF BLADDER CANCER

(71) Applicant: NANOMEDTRIX, LLC, Iowa City, IA (US)

(72) Inventors: Joe G. Assouline, Coralville, IA (US); Sean K. Sweeney, Coralville, IA (US)

(73) Assignee: NANOMEDTRIX, LLC, Coralville, IA (US)

( * ) Notice: Subject to any disclaimer, the term of this patent is extended or adjusted under 35 U.S.C. 154(b) by 236 days.

(21) Appl. No.: 17/069,531

(22) Filed: Oct. 13, 2020

(65) Prior Publication Data

US 2021/0113716 A1    Apr. 22, 2021

Related U.S. Application Data

(60) Provisional application No. 62/931,440, filed on Nov. 6, 2019, provisional application No. 62/916,028, filed on Oct. 16, 2019.

(51) Int. Cl.
*A61K 49/18* (2006.01)
*A61K 49/00* (2006.01)
*A61K 49/16* (2006.01)

(52) U.S. Cl.
CPC ...... *A61K 49/1824* (2013.01); *A61K 49/0089* (2013.01); *A61K 49/16* (2013.01)

(58) Field of Classification Search
None
See application file for complete search history.

(56) References Cited

U.S. PATENT DOCUMENTS

2015/0125398 A1* 5/2015 Assouline .......... A61K 49/1818
424/9.5

OTHER PUBLICATIONS

Sweeney et al. Peptide-Mediated Targeting Mesoporous Silica Nanoparticles: A Novel Tool for Fighting Bladder Cancer. 2017 J. Biomed. Nanotechnol. 13: 232-242. (Year: 2017).*
Bara et al., J. Am. Soc. Echocardio., 19:563 (2006).
Bernardo et al., W. E. Annals of the New York Academy of Sciences, 1176:101 (2009).
Casciaro et al., Invest. Radiology, 45:715 (2010).
Chelliah and Senior, Curr. Card. Rep., 11:216 (2009).
Cormode et al., Nano Lett., 8:3715 (2008).
Giri et al., Angewandte Chemie (International ed.in English), 44:5038 (2005).
Gregory et al., J. Biol. Chem., 278:28067 (2003).
Gregory et al., J. Biol. Chem., 280:2309 (2005).
Gronthos et al., Blood, 84:4164 (1994).
Gruenhagen et al., Applied Spectroscopy, 59:424 (2005).
Hainfeld et al., Br. J. Radiol., 79:248 (2006).
Hsiao et al., Small (Weinheim an der Bergstrasse, Germany), 4:1445. (2008).
Kwon et al., App. Surf. Sci., 254:4732 (2008).
Lai et al., J. Am. Chem. Soc., 125:4451 (2003).
Lauffer, Chem. Rev., 87:901 (1987).
Liang et al., IEEE Engineering in Medicine and,Biology Society In Principles of magnetic resonance imaging: a signal processing perspective / Zhi-Pei Lian; SPIE Optical Engineering Press; IEEE Press: Bellingham, Wash.: New York, NY:, 2000.
Mallidi et al., Conference Proceedings: Annual International Conference of the IEEE Engineering in Medicine and Biology Society. IEEE Engineering in Medicine and Biology Society.Conference, 2009, 2009, 6338-40.
Rabin et al., Nat. Mater., 5:118 (2006).
Radu et al., J. Am. Chem. Soc., 126:13216 (2004).
Simmons et al., Blood, 78:55 (1991).
Slowing et al., J. Am. Chem. Soc., 128:14792 (2006).
Slowing et al., J. Am. Chem. Soc., 129:8845 (2007).
Torney et al., Nat. Nanotechnol., 2:295 (2007).
Webster and Clark, In Medical instrumentation: application and design / John G. Webster, editor; contributing; Wiley: New York:, 1998; vol. 3rd ed.
Yu et al., Chem. Rev., 99: 2353 (1999).
Zhao et al., ACS Nano, 5:1366 (2011).
Zhao et al., J. Am. Chem. Soc., 131:8398 (2009).
Delorme et al., The Concept of Mesenchymal Stem Cells, Clinical Report, Jul. 2006, p. 497+, vol. 1, No. 4, Future Medicine Ltd.
Simmons et al., Advances in Bone Marrow Purging and Processing: Fourth International Symposium, 1994, 271-280, Wiley-Liss, Inc.

* cited by examiner

*Primary Examiner* — Jennifer Chin
(74) *Attorney, Agent, or Firm* — SHUTTLEWORTH & INGERSOLL, PLC; Jason R. Sytsma (57) ABSTRACT

Mesoporous silica nanoparticles (MSNs) that may be useful as ultrasound contrast agents for detecting and treating bladder cancer are described herein. The MSNs include a lanthanide, a fluorophore, and an agent detectable by ultrasound.

15 Claims, 8 Drawing Sheets

| Structure | Clone # | Peptide Sequence | | | | | | | | | | |
|---|---|---|---|---|---|---|---|---|---|---|---|---|
| Heterocyclic | 1, 2, 8, 9 10, 11, 14, 16, 17, 18 | S | I | S | L | G | C | W | G | P | F | C | (GS)4 |
| | 3 | S | V | S | L | G | C | F | G | P | W | C | (GS)4 |
| | 4, 19 | S | I | G | L | G | C | W | G | P | F | C | (GS)4 |
| | 5 | S | V | S | L | G | C | W | G | L | F | C | (GS)4 |
| | 7 | S | V | S | L | N | C | W | G | I | A | C | (GS)4 |
| | 12, 20 | S | M | S | L | G | C | W | G | P | W | C | (GS)4 |
| | 13 | S | I | S | L | G | C | F | G | R | F | C | (GS)4 |
| | Consensus | | α | S | L | G | C | W | G | P | ϕ | C | |
| Cyclic | 6 | S | C | V | Y | A | N | W | R | W | T | C | (GS)4 |
| | 15 | S | C | V | Y | S | N | W | R | W | Q | C | (GS)4 |
| | Consensus | | C | V | Y | x | N | W | R | W | x | C | |

α=aliphatic residues, ϕ=Phe or Trp, x=any amino acid

POROUS NANOCARRIERS FOR THE MONITORING AND TREATMENT OF BLADDER CANCER

STATEMENT REGARDING FEDERALLY SPONSORED RESEARCH

This invention was made with government support under 1R43CA232778-01 and 2R44CA232778-02A1 awarded by the National Institutes of Health, National Cancer Institute, and Small Business Innovation Research (SBIR). The government may have certain rights in the invention.

BACKGROUND OF THE INVENTION

Transitional Cell Carcinoma (TCC) of the bladder affects more than 81,000 new patients in the United States and with over 17,000 deaths predicted for 2019, it accounts for almost 5% of all tumors diagnosed[1] and an estimated $4.7 billion annual cost[2]. Much of this cost (monetary, pain and suffering) is associated with the long-term screening following therapy. Initial screening for bladder cancer is warranted when patients present with hematuria (blood in urine), pain in the back or pelvis, or painful urination. Chief among the impetus to find better screening methods is that, although the majority of human bladder cancer is superficial at the time of detection, the recurrence rate and the risk of progression to advanced disease are high[3-8].

Given the public health importance of this devastating disease, new and technically advanced methods are slow to emerge and must be expedited. A number of accepted approaches are used clinically including: transurethral resection and attenuated *Bacillus* Calmette-Guerin (BCG) immunotherapy. However these methods have recurrence rates of up to 70%[4,6,8] and 50%[3,5,7] respectively. Injection of BCG is fraught with technical pitfalls, laden with pain and prone to cause major urinary tract infections (UTI) which may lead to sepsis and death[9,10].

Other nanoparticle treatments have been attempted for use in bladder cancer, with mixed results[11-16]. For example, because BCG immunotherapy is contraindicated in a significant proportion of patients who are immunocompromised, groups have packaged attenuated forms of BCG into nanoparticles for delivery[11,14]. Unfortunately, these have proven to be less effective at stimulating an immune response than the live form of the bacteria. Nanoparticles based on gold and other biocompatible metals have been used for photothermal therapy, in which emitted light causes a cytotoxic release of thermal energy[15,16]. By the nature of their mode of action, these types of particles require extreme specificity to destroy only tumor cells and leave normal epithelia unharmed. Many forms of nanoparticles are used as carriers of chemotherapeutics[12,13]; these, however, often cannot be visualized/detected and have poor retention in the bladder. Thus it is clear that any diagnostic or therapeutic to be used in the bladder must 1) react quickly with the bladder cancer, and 2) be retained through multiple cycles of bladder filling and emptying.

The present invention describes a nano-based technology which lays the groundwork for the proof-of-concept of the invention's carrier as a tool for labeling bladder cancer through in vitro and in vivo studies[17,18]. The design and manufacture of the multifunctional mesoporous silica nanoparticle (MSN) was carried out with the express purpose of being biocompatible and non-toxic. Thus, individual components were chosen which would maintain biocompatibility in the final form. The silica core is largely bioinert; studies to determine the toxicity of MSN injected intravenously found a lethal dose ($LD_{50}$) of more than 1 g/kg, far higher than any dose needed for imaging studies[19]. Another group found the viability remained high (>90%) in endothelial cell cultures at exposures above 100 µg/mL[20]. The $Gd_2O_3$ component is far less reactive than free $Gd^{3+}$ ions, which are still clinically permitted in most cases in the form of chelates[21,22]. Fluorophores (FITC/TRITC) are used clinically as tracer dyes for various procedures[23,24], and poly (ethylene glycol) (PEG) is a common ingredient in mild laxatives, though at much higher concentrations[25]. Furthermore, it is important to note that the bladder epithelium is mostly non-reactive with respect to absorption of material into the bloodstream; only 3-4% of low molecular weight chemotherapeutics injected into the bladder typically enter the circulation[26-28].

The manufactured MSN of the invention were previously found to preferentially bind bladder cancers in vivo relative to normal bladder epithelium. In order to further improve binding and retention of particles, the invention introduces an additional functionalization of the particle with a bladder cancer cell specific peptide. The use of targeting molecules on the MSN to improve nanoparticle specificity leads to a number of potential positive attributes. With improved accuracy, less material is needed, thus the exposure to the patient is reduced. Specificity also improves retention of therapeutics, which is important in the bladder where normal urination removes any soluble drugs. Here, a "fast on, slow off" approach is needed-the particles must selectively bind the tumor rapidly, and be able to interact with the target for an extended time. However, conferring specificity onto a nanoparticle comes with many challenges. Often, antibodies are used in pre-clinical trials which take advantage of cell surface markers that are overexpressed in cancer cells[16,29]. These have resulted in little success and very little hope for the future clinical use, as most monoclonal antibodies are initially generated in rodents and thus are incompatible with human trials.

For these and other reasons, there is a need for the present invention.

SUMMARY OF THE INVENTION

The invention provides a porous nano-size carrier with a unique capability for bladder tumor monitoring, and for controlled delivery of bioactive materials including antimitotic agents or immunogenic substances. The carrier elicits a significant signal compared to organs, tissues and cells examined with computed tomography (CT), magnetic resonance imaging (MRI), echography as well as fluorescence microscopy.

In general, the carrier may range from about 150-250 nm in diameter, with tunable 3-5 nm pores that may be loaded with anti-tumor drug or reagents including but not restricted to molecular RNA (siRNA) or immunogenic reagents. In one embodiment, the carrier has a diameter of about 200 nm. The carrier can be further functionalized, e.g., with lanthanides (Europium EU, Terbium Tb). For example, the surface and/or the silica framework of the carrier may be covalently functionalized with one or more of the following materials: gadolinium oxide, gold, bismuth, iron oxide, —$CF_3$ functional groups, and/or a fluorophore such as FITC or Texas Red. These materials can then be detected with one or more of the following imaging modalities: MRI, x-ray computed tomography, ultrasound/photoacoustic imaging, and/or fluorescence microscopy. The carrier gain entry into a variety of cells through nonspecific (engulfed) or specific (e.g., via extracellular binding molecules) methods.

Thus, the invention provides a carrier useful, for instance, as an ultrasound contrast agent. The carrier is highly porous and biocompatible, and may incorporate gadolinium oxide nanoparticles in the silica matrix. Alternatively, other substances may be incorporated into the silica matrix including, but not limited to, gold, bismuth, or iron oxide. Such substances may further be cofunctionalized with a biolabel and/or one or more imaging agents, e.g., a contrasting agent, and/or capped with iron, gold, or bismuth. In one embodiment, the MSNs may also be functionalized with poly (ethylene glycol) (PEG) to enhance biocompatibility. Other organic polymers include, but are not limited to, polylactic acid (PLA), poly(lactic-co-glycolic) acid (PLGA), and polyacrylate. Additionally, functionalization with amino acids or polypeptides can enhance biocompatibility. These are lysine/poly-L-lysine, glutamine, glutamate, RGD peptide (arginine-glycine-aspartate). In one embodiment, the carriers are also functionalized with trifluoropropyl moieties ($-CH_2-CH_2-CF_3$, abbreviated $-CF_3$) to enhance ultrasound contrast.

BRIEF DESCRIPTION OF THE FIGURES

FIGS. 1A-C illustrate the kinetics of fluorescent carriers added to human (undifferentiated cells) mesenchymal stem cells (FIG. 1A). Pictures were taken at the indicated times following addition of carriers to the growth medium at 125 μg/mL. Carriers can be seen randomly distributed after 1 hour, binding to the cell surface at 7 hours, and internalized on subsequent days. Scale bars indicate 25 μm. Plot of labeled cell growth tracked during experiment (FIG. 1B). Cells grew in a manner consistent with unlabeled cells, growing to confluence in about 10 days before leveling off. Plot of 2 different measures of particle uptake using two different image processing strategies (FIG. 1C). In one, the quantity of carriers inside and outside cells was measured (blue), and in the other, the number of cells possessing at least one vesicle of carriers is measured (red).

FIGS. 2A-C illustrate powder X-ray diffraction patterns after surfactant removal. The intense peak at 2.5 2θ is characteristic of hexagonally arranged pores. (C) Transmission electron micrograph of synthesized carrier, with (D) higher magnification inset, and (E) expanded-pore carriers. Visualized particles had a uniform size distribution and showed no formation of aggregates. (F) Cells in culture that phagocytose carriers show no adverse effects of tagging. Note: Nitrogen sorption analysis of carriers exhibit Type IV isotherms, consistent with mesoporous particles. The Brunauer-Emmett-Teller (BET) surface area was calculated to be 493 $m^2g^{-1}$ and the average pore diameter for carriers by Barrett-Joyner-Halenda (BJH) calculation is 38 Å, for a specific pore volume of 0.35 cc/g. In addition, dynamic light scattering of the particle in its final configuration shows a mean hydrodynamic diameter of 227.8 nm. Scale bars: 100 nm (C-E); 10 μm (F).

(FIG. 4B) The measured MRI values for each region shown. Error bars indicate standard deviation; *-when compared using the two one-sided T-test of equivalence, the intensity of labeled tumor in the left flank and bladder were not equivalent to the non-labeled tumor and bladder wall (p<0.0001).

FIG. 5A-H illustrate valuation of increased contrast and histopatholgical benefits of our nanoparticle technology. The carriers bind preferentially to bladder cancer cells relative to normal bladder epithelia in vivo as shown in a series of renderings of $T_2$-weighted MRI scans acquired before (FIGS. 5A-C) and after (FIG. 5D F) intravesicular instillation of carrier. (FIGS. 5A and 5D) 2 dimensional grayscale view, the tumor (T) is shown before and after injection of carriers; note clear labeling of the tumor surface (*). (FIGS. 5B and 5E)(B, E) 3-dimensional rendering provides further evidence of the carrier distribution on the tumor surface. (FIGS. 5C and 5F) Here the tumor is segmented and rendered with a pseudo color map. Fingerlike projections are revealed which are not observed before the injection of carriers (FIG. 5C). Histology confirm anatomical observations and particle penetrations in the structures within the tumor: bright field (FIG. 5G) and fluorescent microscopy (FIG. 5H). Scale bars: 1 mm (FIGS. 5A-F); 250 μm (FIG. 5G H).

(FIG. 6C) Membrane proteins were isolated from MB49 bladder cancer and NIH3T3 fibroblast cell lines, plated, and exposed to carriers containing $Gd_2O_3$ and FITC, with or without cyc6 and with or without casein to block non-specific binding (blocking solution: 5% milk powder in PBS). After washing away unbound particles, the FITC fluorescence intensity was measured. The addition of cyc6 increases the level of binding by 16% over carriers without cyc6, and by 70% over casein-blocked membranes. Error bars indicate standard deviation (*-p<0.025; **-p<0.05; †-p<0.0001 for pairwise comparisons between data with matching symbols). Scale bar=10 μm.

(FIG. 8A) Carriers were loaded with siRNA (1.1 nmoles/mg) and release measured by UV-Vis spectroscopy (260 nm Abs.), with release occurring in 50 min. (red). When capped with low melting point gelatin (230 nm Abs), release occurred in 3 h, better coinciding with the timing of cellular uptake. (FIG. 8B) Time course of CBD release from MSN in vitro. In methanol, release was complete within 3 h. In saline, release of 50% CBD occurred in the first 2 h, with maximal release in 24 h.

DETAILED DESCRIPTION OF THE PREFERRED EMBODIMENT

As a novel intravesical treatment for bladder cancer, nanocarriers such as mesoporous silica nanoparticle (MSN)

materials have continued to attract significant interest as drug and gene delivery vehicles that can be cofunctionalized with a biolabel or contrasting agent (Giri et al., 2005; Gruenhagen et al., 2005; Hsiao et al., 2008; Kwon et al., 2008; Lai et al., 2003; Radu et al., 2004 UPDATED REFS). MSNs are highly porous, biocompatible materials that have proven to have potential pharmacological applications. The MSN offer several characteristics that make it unique to other nanomaterials. These advantages include high surface area, tunable pore size and pore volume, and two independently functional surfaces, an exterior surface and interior pore surface.

The invention provides a mesoporous silicate body (particle) having one or more pores, and two or more functionalizations. The mesoporous silicate body can be a spherule having a diameter of about 40 nm to about 600 nm, about 100 nm to about 300 nm, about 150 nm to about 250 nm, about 300 nm to about 600 nm, or about 500 nm to about 4 µm. The mesoporous silicate body can also be a rod having a length of about 500 nm to about 1 µm, about 400 nm to about 600 nm, or about 50 nm to about 250 nm. The rods can have various diameters, typically from about 50 nm to about 500 nm. The pores of the MSN can be about 1 nm to about 50 nm in diameter, e.g., less than about 30 to about 50 nm in diameter, and can be about 1 nm to about 10 nm, or about 1 nm to about 5 nm, in diameter.

The mesoporous silicate bodies may have removable caps, which can include inorganic and/or organic molecules, e.g., for imaging or intravesical drug delivery. In one embodiment, the removable cap is gelatin derived from mammalian collagen, having a melting point of about 35 degrees Celsius to about 45 degrees Celsius. In another embodiment, the removable cap is a synthetic phospholipid bilayer, comprised of one or more types of fatty acids and cholesterol.

The particles of the invention are useful for intravesical therapeutic drug delivery and for tumor monitoring using medical imaging modalities. In one embodiment, the MSNs of the invention include a lanthanide such as gadolinium. Gadolinium has gained popularity as an MRI contrast agent because, like iron oxide, it affects large changes in the local magnetic fields where it is present. By virtue of the fact that it has 7 unpaired electrons in its outer shell, it interacts very efficiently with surrounding protons. If the same specimen is scanned at two different echo times, the changes in field effects between the two scans is larger relative to the differences between background materials. Therefore, a simple subtraction of one image at one echo time from the other further enhances the tracing of the material.

Magnetic Resonance Imaging (MRI)

Magnetic resonance imaging uses small variations in the magnetic field arising from differing proton spin densities p(x,y) in tissue to generate its images. Briefly, the grayscale value at each pixel in a slice of an MR image is the 2-dimensional inverse Fourier transform of that slice's k-space, or frequency domain s(t). The radio frequency (RF) data encoded in the frequency domain is collected when small perturbations are made in the larger magnetic field of the MR scanner using smaller gradient coils that vary over time as $G_x(t)$ and $G_y(t)$. The general equations describing the signal are $$s(t) = \int_{-\infty}^{\infty}\int_{-\infty}^{\infty} \rho(x, y)e^{-j2\pi[k_x(t)x+k_y(t)y]}dxdy,$$

where $$k_x(t) = \int_0^t \frac{\gamma}{2\pi}G_x(\tau)d\tau, \text{ and}$$

$$k_y(t) = \int_0^t \frac{\gamma}{2\pi}G_y(\tau)d\tau.$$

The MR signal of a specific tissue can also be described by its parameters ($T_1$, $T_2$, $T_2^*$ relaxation times) and the parameters of the scan (repetition time TR, echo time TE, and/or flip angle α). After a material is magnetized with a certain flip angle α, the magnetic field in the longitudinal axis $M_z$ decays (relaxes) with time constant $T_1$, and varying the time between pulses (repetition time $T_R$), tissue with different $T_1$ relaxation times show up with different levels of intensity in the reconstructed image. This is known as a $T_1$-weighted image. In a $T_2$-weighted image, the echo time $T_E$ (the time between the pulse and the midpoint of signal readout) is used to generate differing intensities between tissues of different $T_2/T_2^*$ relaxation times (the time constant of relaxation or "de-phasing" in the transverse plane, or $M_{xy}$) (Liang and Lauterbur, 2000).

Besides varying $T_R/T_E$ on the scanner to achieve the desired contrast, additional contrast can be achieved by using one of several contrast agents. MRI contrast agents are ferromagnetic, paramagnetic, or superparamagnetic materials which interact with the protons present in the surrounding medium, thereby altering the apparent $T_1$ or $T_2$ relaxation time. The effect of contrast agents on the observed $T_1$ or $T_2$ value is given by the equation $$\frac{1}{T_{obs}} = \frac{1}{T_{tissue}} + r[\text{contrast}],$$

where $T_{obs}$ is the observed $T_1$ or $T_2$ value, $T_{tissue}$ is the actual $T_1$ or $T_2$ relaxation time of the tissue being scanned, r is the $r_1$ or $r_2$ relaxivity of the contrast agent, measured in $s^{-1} \cdot mM^{-1}$, and [contrast] is the molar concentration of the contrast agent (Lauffer, 1987).

Most ferromagnetic contrast agents involve the use of superparamagnetic iron oxide (SPIO), which perturbs the tissue's local magnetic field, causing a change in $T_2$ or $T_2^*$ relaxation time.

In MRI, the signal-to-noise ratio (SNR) is proportional to the magnetic field, the voxel size, and the square root of total scan time. Compared to the above scan parameters, the magnetic field of a clinical scanner is reduced by a factor of 3, the voxel size is increased by a factor of about 2, and the scan time is reduced by as much as 8 times (from up to 4 hours to about a half hour). Therefore, the reduction in signal can be estimated as $2/(3\sqrt{8})$, or about 4.2 times smaller. This can be approximately balanced out by increasing the number of labeled cells from the $5\times10^4$ that was detected in the above scans to about $2\times10^5$. For both of these estimations, the actual thresholds are likely to vary from these estimates, and for different tissues, and can and should be confirmed through testing of scaled-up phantoms in the clinical scanners at a time when clinical testing is more imminent.

X-Ray Computed Tomography (CT)

In one embodiment, the MSNs of the invention include an electron-dense element such as gold. Because of its density and non-reactivity, gold is a commonly used CT contrast agent. Unlike MRI in which the contrast is derived from magnetic properties of tissue, CT images are essentially based on the density of the tissue in the path of the x-rays. In summary, x-ray photons at a known energy are projected towards the patient and detected on the other side. The simplified equation of intensity of the photons striking the detector is given by the relationship $$I(x)=I_0 e^{-\mu x},$$

where $I_0$ is the initial intensity and $\mu$ represents the attenuation coefficient of the material (a function primarily of tissue density). In order to generate a multislice CT image, this principle is expanded to a 2 dimensional detector which can be rotated around the body. Many 2-D projections are compiled into a 3-D image according to the equation $$I^{\theta k}=I_0 e^{-\Sigma_{ij} w_{ij}^{\theta k} \mu_{ij}},$$

where $I^{\theta k}$ is the intensity data for detector position k and angle $\theta$, $w_{ij}$ is a weighting value for position (i,j) on the detector at position k and angle $\theta$, and $\mu_{ij}$ is the attenuation of the material at position (i,j) (Webster and Clark, 1998).

In x-ray CT, contrast agents are effective if they have an ability to greatly change the x-ray opacity of the tissue of interest. Therefore most of the early contrast agents were based on heavy elements such as iodine and barium. Because of toxicity concerns, these agents have evolved over time, and other contrast agents based on electron-dense metals have also been studied, and are well reviewed by Yu/Watson. Of the heavy metal contrast agents, those based on gold, bismuth and gadolinium appear to be the most studied (Yu et al., 1999).

The efficacy of gadolinium compounds in MRI is well-established; as a CT contrast agent, the quantity of research is more limited, but shows that it can indeed alter the opacity of surrounding tissue. Englebrecht, et al (*Rofo*, 1996 165 (1):24-8) showed that Gd-DTPA (Magnevist®) caused roughly ⅓ the attenuation as an equivalent concentration of Iohexol 300, an iodinated CT contrast agent. To attain the same attenuation, tripling the concentration of Magnevist® exceeded its maximum recommended dose. However, the Magnevist® was successful in highlighting vascularization for a short time, enabling imaging of highly vascularized tissue such as the liver.

Zwicker et al (*Investigative Radiology* 1991 26:S162) showed that at a tube voltage to 120 kVp (whereas a typical CT scan is about 75 kVp), the attenuation of Magnevist® is comparable to that of iodinated CT contrast agents. The added benefit of using CT at 120 kVp compared to 75 kVp is that it reduces the radiation absorbed by the patient by a factor of about 3. Research in gadolinium CT appears to have stopped abruptly as cases of nephrogenic systemic fibrosis (NSF) were linked to gadolinium contrast agents; however, newer agents are much less likely to allow freely moving gadolinium ions which caused NSF, so this may be a fertile territory to carefully explore again.

Ultrasound

In one embodiment, the carriers are functionalized with trifluoropropyl moieties ($-CH_2-CH_2-CF_3$, abbreviated $-CF_3$) to enhance ultrasound contrast. Ultrasound is perhaps the fastest and safest way to obtain in situ images, as it requires only a few seconds of preparation with ultrasound gel and produces no ionizing radiation. The drawback is that the spatial resolution does not approach what is possible in CT or MRI at this time. In this modality, a piezoelectric transducer produces sound at high frequencies (typically between 2 and 15 MHz for clinical applications and up to 40 MHz or more for research applications) and generates an image based on the timing of echoes returning to the transducer. Echoes are generated when the propagated sound wave strikes an interface between volumes with differing acoustic impedances (Z) and part of the sound wave reflects back to the transducer. Acoustic impedance is defined as $$Z=\rho c,$$

where $\rho$ is the density and c is the speed of sound in the tissue[30]. At the interface between two tissues, the reflectance coefficient (R) describes the fraction of sound energy that will be reflected back to the transducer. The remaining fraction continues propagating deeper into the tissue where it may strike another interface. R is related to the acoustic impedances of the two tissues at the interface ($Z_1$ and $Z_2$) according to the equation $$R=\left[\frac{Z_1-Z_2}{Z_1+Z_2}\right]^2.$$

These principles are applied to the generation of ultrasound images. In A-mode imaging, one transducer is used to plot all the tissue boundaries along one axis as a function of time. One application of A-mode imaging is tracking opening and closing of heart valves or movement of a ventricle during the heart cycle in echocardiography. In B-mode imaging, an array of transducers is coordinated to form a 2D image. This may be the most common way ultrasound is used, and includes fetal sonography among other applications. Newer ultrasound systems are capable of Doppler mode, in which frequency shifts in the sound wave are used to calculate blood flow through arteries, and even 3D ultrasound, in which the transducers are swept across many 2-D fields in rapid succession to generate a 3-dimensional image (Webster and Clark, 1998).

Exemplary Tumor Modeling and Imaging/Image Processing Parameters

All procedures were performed according to NIH guidelines and previously approved by the Institutional Animal Care and Use Committee (IACUC). Intravesicular instillation of tumor cells was performed according to previously described methods[31]. Female C57Bl/6 mice were anesthetized with a ketamine/xylazine mixture. The bladder was chemically burned by instillation of 5 μL 0.2 M silver nitrate, followed by rinsing with 100 μL phosphate buffered saline (PBS). A 50 μL suspension containing 5×10⁵ MB49-Luc⁺ cells in 50% normal mouse serum was instilled into the bladder and retained for one hour by catheter exclusion. Additional boluses of 1×10⁵ tumor cells were injected subcutaneously in the left and right flank. In initial experiments designed to determine maximum signal, cells were labeled with MSN prior to instillation; in later studies designed to be more clinically relevant, the tumor was established prior to instillation of free MSN particles (1 mg MSN/50 μL PBS). Negative control mice were instilled with sham (saline) injections, followed by instillation of free MSN following the same timing as tumor mice.

Imaging/Image Processing

Images were acquired 24 hours after instillation of particles to allow for the elimination of free particles through urination. From 1-8 days following tumor implantation, in vivo fluorescence and luminescence was measured using the IVIS 200 with appropriate settings for detection of GFP, TRITC, and luciferase activity following intraperitoneal injection of 1.5 mg luciferin. MRI scans were acquired using the Unity/INOVA 4.7 T small animal scanner (Varian, Palo Alto, Calif.) with a 25 mm gradient RF coil and fast spin echo multislice (fsems) sequences with $T_1$- or $T_2$-weighting (T1-weighted scans: $T_R$=800 ms, $T_E$=15 ms, echo train length=8, number of averages=10; $T_2$-weighted scans: $T_R$=2000 ms, $T_E$=15 ms, echo train length=8, number of averages=10). Typical image dimensions are 512×512 with 30 slices and a voxel size of 0.068×0.068×0.4 mm. Scans were saved as DICOM image stacks, which were converted to NIFTI format and preprocessed using a MATLAB routine developed in the lab, following a method of background removal[32] and interpolation by reverse diffusion[33]. Using the free medical image processing software MIPAV, scans were normalized to one another by assigning a value of 1000 to the average intensity of fat adjacent to the kidneys, with all other values linearly interpolated between 0 and 1000. Volumes of interest (VOIs) were either manually drawn or semi-automatically selected using the "levelset VOI" tool in MIPAV.

Histopathology and Statistical Analyses

Following the MRI scans, mice were euthanized by $CO_2$ inhalation. The bladders were excised, embedded in OCT medium, flash frozen in liquid nitrogen and sectioned. A portion of the sections were mounted on glass slides without stain for use in fluorescence microscopy, while adjacent sections were stained with hematoxylin and eosin for histological analysis. Fluorescence images were acquired using standardized camera settings (Olympus DP70 camera, 1360×1024 resolution, and 15 second exposure time), while corresponding bright field images were acquired using the same resolution and the camera's auto-exposure setting with color correction. The average red fluorescence intensity of each 10× field was quantified by isolating the red channel and using VOI tools to isolate regions of tissue from the background, using the bright field images as a reference for identifying the tissue and background. The average fluorescence intensity of each image was normalized by dividing it by the average intensity of the background. Comparisons of measurements between groups of mice were made using Student's unpaired T-test with an alpha level of 0.05 considered significant. Comparisons of different tumors within the same mouse were made using a two one-sided t-test (TOST)[34] with a significance level of $\alpha$=0.05 and a test margin of 0.05 (a unitless value of normalized MRI intensity), representing the average smallest difference between two intensities that our image processing technicians could discern with the naked eye.

The invention will be further described by the following non-limiting examples.

Example I

Figure 1A:
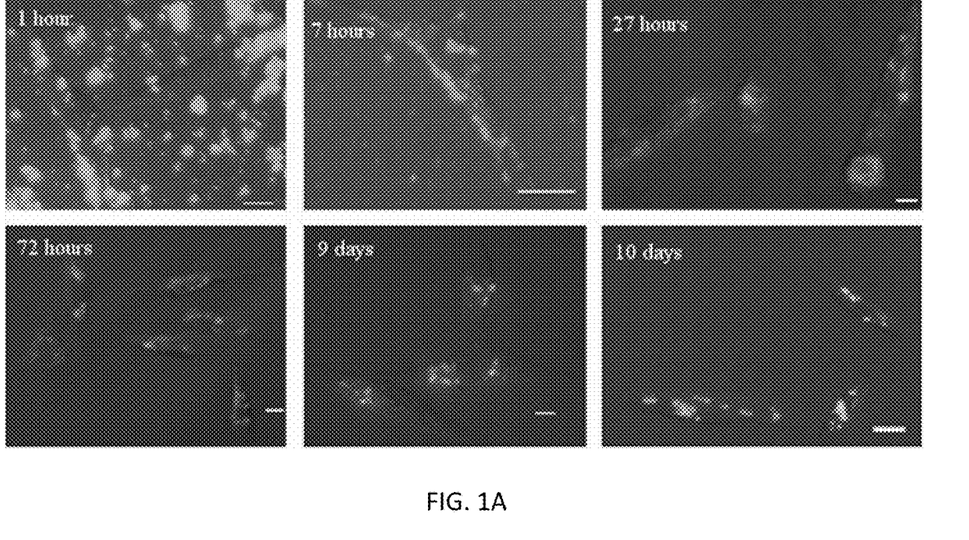
Figure 1B:
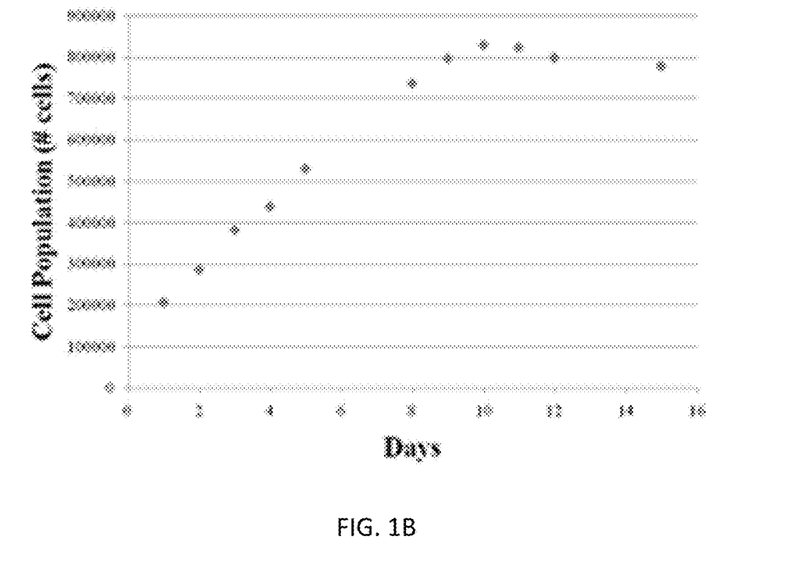
Figure 1C:
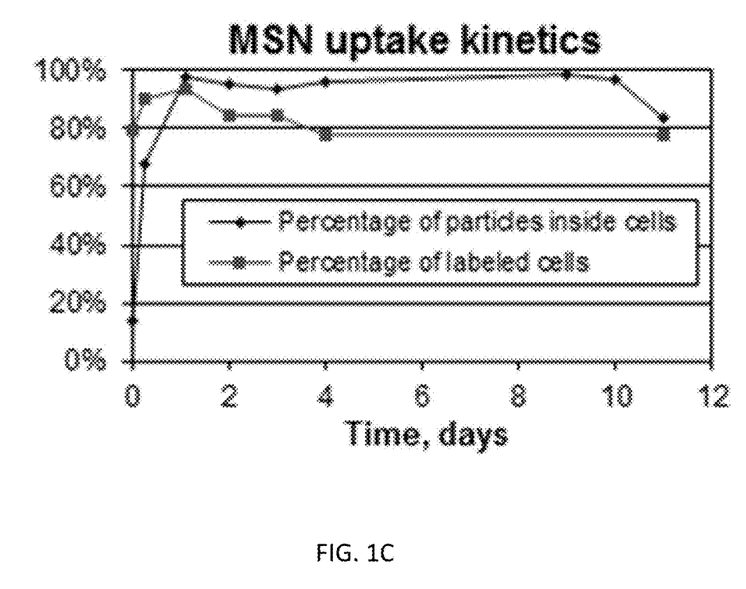
Figure 2A:
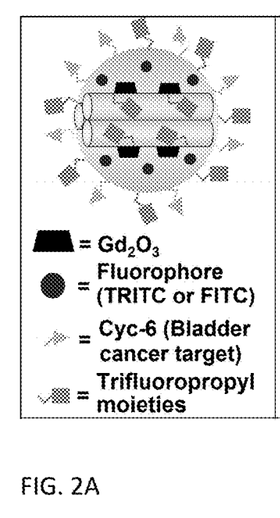
Figure 2B:
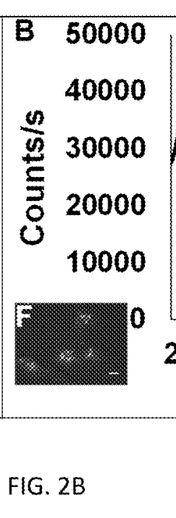
Figure 2C:
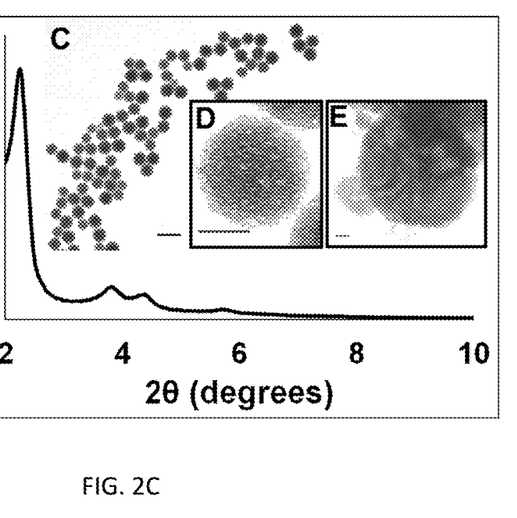
Figure 3:
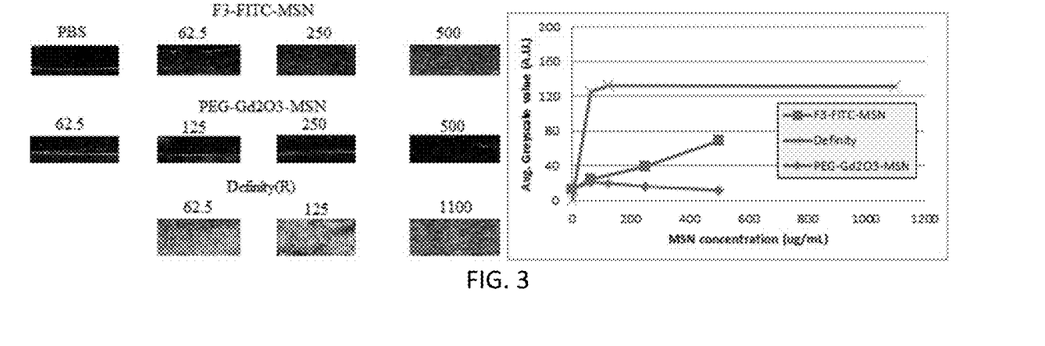
FIG. 3 illustrates ultrasound scanning of agars containing PEG-coated $F_3$-FITC-$Gd_2O_3$-MSN or PEG-$Gd_2O_3$-MSN at varying concentrations, in μg/mL (A). The grayscale values were compared with those for Definity®, a commercially available ultrasound contrast agent (B).

Multifunctional MSN was synthesized for in vivo imaging of bladder tumors according to the schematic (FIG. 2A). By incorporating $Gd_2O_3$ into the silica matrix and covalently grafting FITC or TRITC onto the particle surface, the MSN is functionalized for fluorescent and MRI imaging modalities. Systematic characterization was performed at each step in the process of synthesizing the PEG-TRITC-$Gd_2O_3$-MSN. Powder XRD analysis confirmed hexagonally arranged mesopores in the diffraction pattern of the $Gd_2O_3$-MSN as evident by the intense $d_{100}$, and well resolved $d_{110}$ and $d_{200}$ peaks characteristic for MSN (FIG. 2B). Transmission electron micrographs of the $Gd_2O_3$-MSN particles showed this pattern as well as uniform size distributions and good dispersibility with little aggregation (FIG. 2C-E, inset). Nitrogen sorption analysis of the TRITC-$Gd_2O_3$-MSN exhibited a Type-IV isotherm, typical of mesoporous materials, with a BET surface area of 710 $m^2g^{-1}$. The average pore diameter for TRITC-$Gd_2O_3$-MSN by BJH calculation is 24 Å. The fully synthesized PEG-TRITC-$Gd_2O_3$-MSN was characterized by DLS; the median hydrodynamic diameter of the particles was 187.3 nm, with 96.3% of the particles falling within the primary distribution peak, spanning between 90 and 400 nm, resulting in a polydispersity index (PDI) of 0.535. The number of particles greater than 400 nm (likely aggregated MSN) are less than 4% of the total and do not have adverse experimental implications on the tagging of bladder tumors. Prior to use in tissue culture or in vivo, the fluorescence (FITC or TRITC) was measured using serial dilutions in a fluorimetric plate reader. In order to eliminate unbound fluorophores from the suspension, the particle suspensions were repeatedly rinsed in phosphate buffered saline and centrifuged until no detectable fluorescence was observed in the supernatant.

Labeling/Flow Cytometry

Particle uptake by TCC cells was determined by flow cytometry. GFP⁻/TRITC⁻ cells were used to establish the threshold for detection while the GFP⁺/TRITC⁻ cells were used to confirm the efficiency of GFP transfection, which was found to be 99.8%. In the final sample, 69.6% of the cells were found to be GFP⁺/TRITC⁺, with a wide range of levels of rhodamine fluorescence, indicating some cells picked up more MSN particles than others.

In Vivo Fluorescence

Implantation of PEG-TRITC-$Gd_2O_3$-MSN-labeled MB49-Luc⁺ and MB49-GFP⁺ cells was confirmed using in vivo luminescence and fluorescence. Using the standard detection methods (luciferin luminescence or GFP fluorescence), the tumor was detectable within 6-8 days in vivo, consistent with previous results. Using the MSN for detection (TRITC fluorescence), the tumors were detectable in 1-4 days. The growth rate was consistent with that of unlabeled tumor cells, indicating that the particles are not inhibitive of tumor growth.

MRI Imaging

We implemented two tumor labeling approaches, representing incremental stages moving towards translational significance. In the first, we labeled cells prior to implantation to determine the maximal MRI signal attainable. Subsequently, we implanted the tumor cells first, labeling them in vivo, to represent a clinically relevant scenario.

Figure 4A:
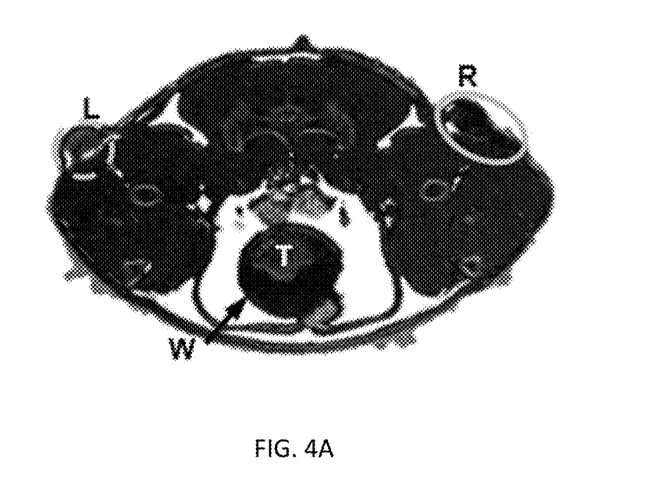
FIG. 4A illustrates (FIG. 4A) A pseudocolor slice of T1-weighted axial MRI data showing definite intensity difference 8 days post injection between the two subcutaneous injections in the thigh (particle labeled cells in the left flank, L, and non-labeled cells in the right flank, R) as well as the tumor within the bladder (in situ) (T) and bladder wall (W).
Figure 4B:
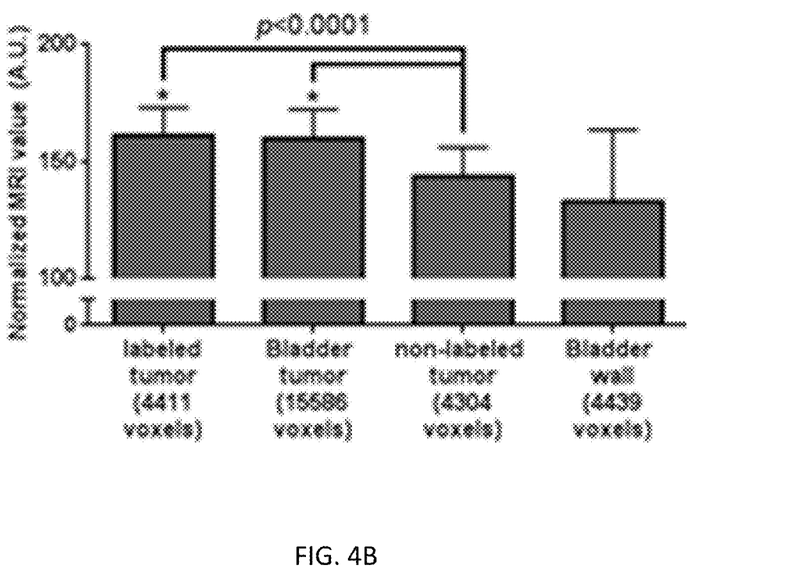
Figure 4C:
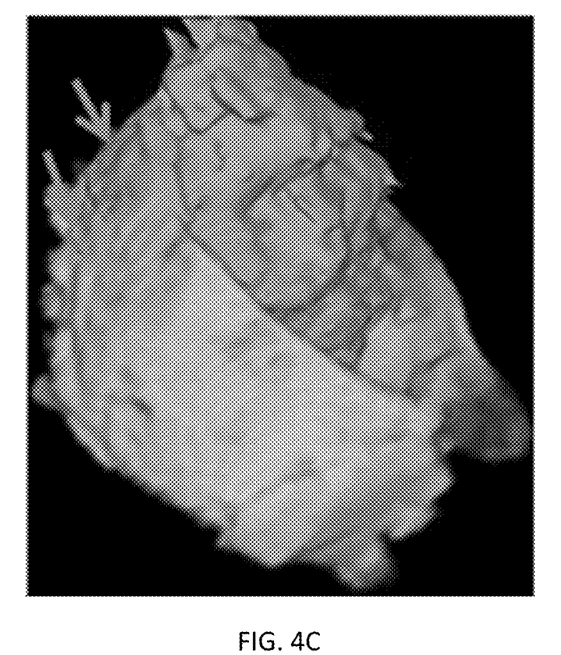
(FIG. 4C) A 3-D virtual cystoscopy rendering of the same tumor in (FIG. 4A) with the tumor identified by fuzzy C-means segmentation (red). Unique features: arrows indicate regions where the tumor has invaded the bladder wall, an important pathological milestone.

1) To determine the maximum MRI signal, MB49-Luc⁺ cells were labeled with PEG-$Gd_2O_3$-TRITC-MSN prior to instillation in the bladder to obtain the best possible contrast in MRI. Tumors were also implanted in the left and right flank, using labeled and non-labeled cells, respectively, as controls. With $T_1$-weighting, a hyperintensity was observed for tumors comprised of labeled cells relative to non-labeled cells (FIG. 4A). After segmentation, the normalized MRI values of labeled (161.2±11.8) versus non-labeled (143.3±12.9) flank tumors were compared using the TOST test for equivalency with a test margin of 0.05 and found to be non-equivalent at a significant (p<0.0001) level (FIG. 4B). Further, the tumor instilled into the bladder (159.5±12.8), also comprised of MSN-labeled cells, was found to be equivalent to the flank tumor comprised of labeled cells (p>0.05) and non-equivalent to the tumor comprised of non-labeled cells (p<0.001). This initial test also confirmed that the process of labeling MB49 cells with MSN did not alter their ability to engraft, either subcutaneously or in the bladder. Three dimensional rendering of the tumor shows infiltration of the bladder wall, potentially metastasizing to nearby tissues (FIG. 4C). This represents clinically important data for tumor staging.

Figure 5A:
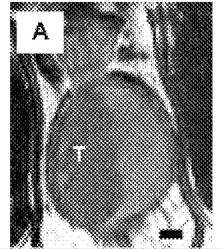
Figure 5B:
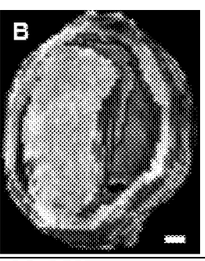
Figure 5C:
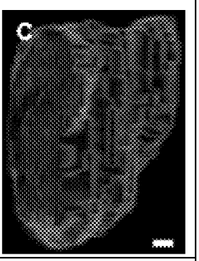
Figure 5D:
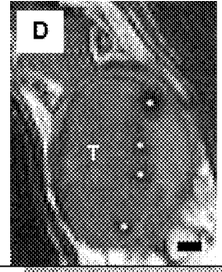
Figure 5E:
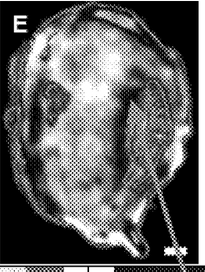
Figure 5F:
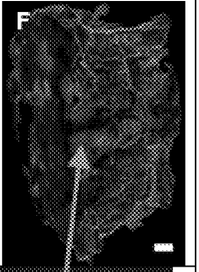
Figure 5G:
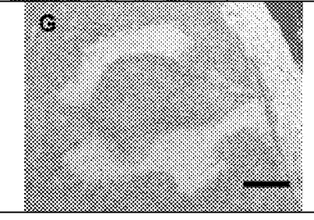
Figure 5H:
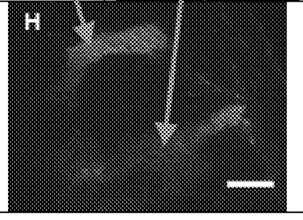

2) To represent a more clinically relevant scenario, we subsequently injected MB49 tumors to establish the tumor, then after 8 days we labeled in vivo via intravesicular instillation of colloidal PEG-$Gd_2O_3$-TRITC-MSN particles (1 mg MSN in 50 μL PBS). MRI scans showed immediately before and one day after MSN addition to determine the qualitative effects of the MSN on tumor characterization as well as the quantitative changes in $T_1$- and $T_2$-weighted MRI signal for bladder tumor relative to normal bladder epithelium. A representative 2-D slice of $T_2$-weighted MRI of the same tumor is shown before (FIG. 5A) and 24 hours after (FIG. 5D) addition of MSN particles. Each pair of images are shown after normalization, using equivalent input-output color maps. Additional 3-D renderings of the tumor in situ (FIG. 5B/E) and segmented (FIG. 5C/F) reveal unique features within the tumor, including fingerlike projections which have a different consistency than the bulk of the tumor and can be traced along the outer boundary. Quantitatively, the animals with tumors showed a much larger magnitude of change in normalized MRI value after administration of particles than the bladder walls of non-tumor, sham-injected negative control mice. This result provides evidence that in vivo tumors take up MSN particles with a higher affinity than normal bladder epithelium. The projections were found to be considerably hypointense in these renderings of $T_2$-weighted scans, indicative that in larger tumors, a subset of cells have an especially high affinity for the MSN.

Histological Analyses

To validate and confirm MRI observations, tissues were processed for histological evaluation. The bladders were excised after the final MRI scans, re-scanned for whole tissue fluorescence signal using the IVIS system, and then serially sectioned. Gross anatomical observations using IVIS show, as expected, only the Luc$^+$ tumor showing luciferase luminescence, while both the GFP$^+$ and Luc$^+$ tumor have positive fluorescence in the red channel, indicating retention of the PEG-$Gd_2O_3$-TRITC-MSN. The fingerlike projections seen in MRI were observed to be regions of higher cell density/faster growth, and are consistent with observations made of TCC in humans[35]. Additionally, the fluorescence micrograph corroborates the MRI scan, showing these are the areas of greatest particle uptake. In both the T1- and T2-weighted MRI scans, we observed clear improvements in boundary delineation. This allowed for the in vivo evaluation of features such as the bladder wall with a level of detail approaching that of histological sections. Based on measurements collected from both MRI and histological sections, we calculated the thickness of the bladder wall to be approximately 1.00 mm, corresponding to 17 pixels at our achievable resolution.

This report documents the findings on an orthogonal mouse model, and the potential for translation to clinical use of a novel nanoparticle-based technology. This approach may improve diagnostic and potentially therapeutic outcomes in transitional cell carcinoma (TCC) of the bladder. Clinically relevant gold standards to use for a comparative basis were not known. Clinical approaches include ImmunoCyt/uCyt™, a fluorescent test that uses three monoclonal antibodies[36], and UroVysion™, which is an in situ hybridization test using four different probes to different chromosomes[37]. The benefits of Hexvix or hexyl aminolevulinate were known, which is similar to a chemical found naturally in the body and contains porphyrins[38]. The underlying principle of this approach is that cancer cells absorb this substance faster than healthy cells and turn fluorescent pink when the cystoscope light changes from white to blue. To date, we have not seen a report of cystoscopy-based approaches used in murine models.

Using the well-established MB49 murine line of bladder cancer cells, the uptake of particles was measured in vitro, followed by non-invasive detection of labeled, implanted tumors in vivo using magnetic resonance imaging. In a pre-clinical animal model for bladder cancer, free particles were instilled in bladders with pre-established tumors. It was demonstrated that the localization of the particles highlighted to the tumor helped delineate its edges and other features which were not otherwise detectable. Fingerlike projections-areas were identified which are consistent with the literature and are believed to be connective cellularized tissue[39]. These tumor penetrating structures displayed a higher particle uptake than the surrounding tumor. It is tempting to envision the potential therapeutic applications of the particles as they are able to access the inner cellular components of the tumor.

Two major hindrances to the recovery and poor prognostics of this form of cancer is the delay in detection of the cancer and its subsequent propensity to rapidly metastasize to adjacent tissue[7,40]. Although TCC is among the most deadly forms of cancer, the methods for diagnosis, including fluorescent and colored dyes that "paint" the bladder wall and delineate the tumor for use with cystoscopic techniques, however, are lacking in both depth of penetration and accuracy[41,42]. Because the depth of tumor penetration is difficult to grade through cystoscopic means alone, the bladder is often removed as a precautionary measure, to the severe detriment of quality of life for the patient[6,43,44]. The present results show a novel option based on a core of MSN for multimodal use in cancer diagnostics. In addition, the potential is clear for the material to be used therapeutically, as a carrier of anti-tumor agents. The engineered nanoparticles are made to improve visualization of the tumor through T1- and T2-weighted computational MRI techniques.

Using the well-established MB49 murine TCC line in culture, it was found that 69.6% of cells to be labeled with our PEG-$Gd_2O_3$-TRITC-MSN, with most cells fluorescing between 2 and 3 orders of magnitude above the detection threshold for the flow cytometry instrument. The particles were well-tolerated by the cells; viability of labeled cells remained high (over 90%) as indicated by trypan blue exclusion dye measurement and by virtue of the successful engraftment of labeled tumor cells in vivo. The manner of uptake has not yet been characterized, though from the literature and our own observation it is most likely that particles are engulfed by phagocytosis. The uptake mechanism of similarly sized and functionalized MSN has been characterized by other groups as co-localized with endosomes[45,46] These studies have examined the involvement of clathrin-coated pits, using inhibition of clathrin to show reduced uptake[47], and lysosomes, using fluorescent lysosomal tracking dyes[45]. Additional determination of uptake awaits future experimentation with specific cell signaling molecules on the MSN surface.

The current standard pre-clinical model for TCC is the mouse orthotopic model in which MB49 murine TCC cells are implanted onto a chemically disrupted bladder epithelium[31]. Although the model presents a number of advantages, i.e., it reliably creates tumors which closely mirror the histological picture of human TCC, we found that the tumor growth varies greatly depending on the quality of the chemical disruption and the number of cells that bind to it. In addition, the small size of this animal model does not lend itself to cystoscopy or other clinically relevant screening techniques. It was shown that by combining the animal model with the image improvement offered by our MSN, we can use small animals (mice) and create valuable virtual cystoscopy. Early experiments involve labeling of cells with our particles prior to implantation in order to optimize our imaging parameters, and to show that labeled cells will engraft and grow in a similar manner to non-labeled tumor cells. Control injections of labeled and non-labeled cells implanted subcutaneously in either thigh of the mouse showed similar growth characteristics, indicating that cell labeling alone did not adversely affect tumor growth or implantation. Importantly, the technology allows for the non-invasive detection of histological features. Within the bladder, the tumor boundary was more easily delineated, and was observed to cross the bladder wall. This crucial data regarding depth of tumor penetration is impossible to obtain clinically through cystoscopy alone[35,39,48].

The experimentation strategy was first to establish a bladder tumor model in which nanoparticles would be most visible and then refine our approach to develop a method with more clinical relevance where the tumor was initiated in the bladder, then followed by injection and binding in vivo of free MSN 8 days later. Interestingly, prior to the instillation of particles, the MRI scan shows a very homogeneous tumor which reflects the uniformity of the MB49 cells in culture. Only after administration of particles are unique heterogeneities revealed, which are correlated histologically. This includes the formation of fingerlike projections, forming largely around the boundaries of the bulk tumor. These regions appear to be more fibroblastic in morphology, with a denser matrix of connective tissue than the bulk tumor, as evidenced by the higher relative amount of eosin staining. Furthermore, these regions have a higher affinity for our MSN than the bulk tumor; this is consistent with our observations, and those of other groups,[46,49] that MSN are readily engulfed by fibroblast cells. To the best of the inventor's knowledge, nothing is published regarding the heterogeneity of MB49 tumors in situ, though groups have reported the presence of fingerlike projections in human clinical pathological specimens.[39]

The typical clinical tool for bladder cancer diagnosis is white light or fluorescent cystoscopy, used in conjunction with a form of dye that improves definition of the tumor boundaries.[50-52] Clinically, MRI virtual cystoscopy of the bladder is less commonly used,[53] and although gadolinium-based contrast agents are sometimes administered intravenously prior to scanning, specific agents that bind tumors are not yet available. Results indicate that intravesicular instillation of MSN particles improves differentiation of the tumor in MRI; the signal obtained from normal bladder wall is unaffected by particle instillation, whereas the signal of the tumor increases under T1-weighted MRI, and decreases under T2-weighted MRI. This is consistent with the accumulation of gadolinium-based contrast agents in tumors, and corroborated by the difference observed in fluorescence signals from excised bladders of tumor and normal mice. In normal bladder epithelia, the particles that were retained appeared to be discretized in macrophages, whereas the tumor tissue possessed a brighter, more widespread fluorescence throughout, or in the case of more heterogeneous tumors, spread among a particular subpopulation of the tumor.

This example takes into account the consideration that clinical efficacy of using nanoparticles may be hindered or diminished due to bladder epithelium becomes hyper-permeable in TCC bladders[54,55]. The immediate implications being that particles may bind to non-tumor regions in a cancerous bladder, thus leading to overestimation of the true tumor size. It was shown that has not been the case in the study, as it was clearly demonstrated that the particles have a predilection for cancerous tissue.

With respect to image quality improvement, the current small animal scanner has a magnetic field of 4.7 T and is capable of in-plane image resolutions below 100 µm. At this resolution, patterns in MRI corresponding to layers observed in histological sections were detected, and visualized folding patterns within the bladder 3-dimensionally. With the advent of MRI systems with magnets as large as 7 T and more powerful gradient coils, both in small animal and clinical use, antian improvement in signal/contrast for the same MSN formulation.

Thus, there is a need to improve with higher-specificity molecules. In addition to advances in imaging technology, the obtained signal can be further improved by increasing the specificity of the particles for bladder cancer cells. The particles presented thus far have not been functionalized for cell specificity; the specificity we observe is a result of exploiting the morphological differences between normal and tumor cells in the bladder. Whereas healthy/intact epithelium is defined by tight gap junctions and cell adhesion molecules only at the basement membrane, diseased (cancerous/inflamed) epithelium divides rapidly, has looser gap junctions, and overexpresses adhesion molecules, such as EpCAM[42,56] integrins,[57] laminin, cadherins,[55] and other surface molecules[58,59]. Due to these features, diseased epithelium has a higher affinity for foreign objects than normal epithelia.

An additional desirable property of MSN particles which was not directly addressed in this study would be to have uptake and delivery of soluble materials within their porous structure. Many have successfully demonstrated delivery of bioactive agents in vitro using MSN[61-64] The increased complexity of delivery in vivo makes it a more challenging scenario[65,66] However, if some of these challenges can be overcome in the harsh chemical environment of the bladder, cancer treatment can be vastly improved. Whereas most chemotherapeutics are quickly eliminated from the bladder via urination[67,68], particles loaded with chemotherapeutics and retained by tumor cells will remain in the bladder for a longer time. Similarly, BCG immunotherapy can be improved through longer retention times, thus improving the depth of drug delivery, rather than simply removing the outermost cells a few layers at a time as current therapies tend to do[40,69].

Example 2

Cyc6-Functionalized MSN Particle Specificity for Bladder Cancer Cells

The bladder cancer cell specific peptide Cyc6 was identified using a phage display library with the filamentous bacteriophage M13. This peptide, and a heterocyclic variant HCl, were found to have nanomolar affinity for bladder cancer cells (Table 1). Tested cells included normal mouse bladder, and two lines of mouse bladder cancer: MB49-1, and MBT-2. Mouse melanoma B16, human prostate cancer LNCaP, and human breast cancer MDA-MB453 were also negative for the protein.

Figures 6A, 6B:
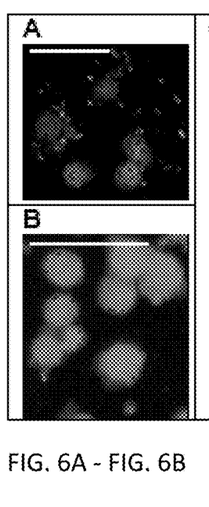
FIGS. 6A-C illustrate that carriers covalently linked with cyc6 peptide demonstrate higher affinity for MB49 cells than carriers alone. MB49 cells were grown on glass coverslips and exposed to carriers containing $Gd_2O_3$ and FITC, with (FIG. 6A) or without (FIG. 6B) cyc6, then washed (merge of red: nuclei stained with acridine orange; and green: particles containing FITC). Clusters of carriers can be seen closely associated with MB49 cells, whereas carriers without cyc6 are considerably sparser.
Figure 6C:
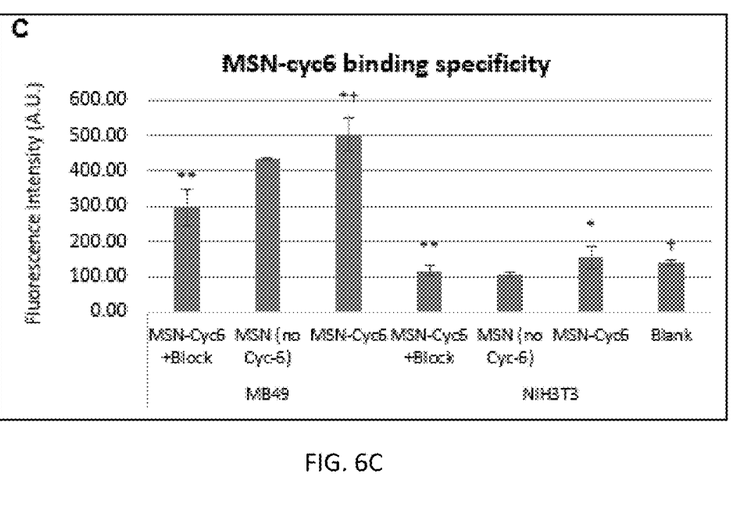
Figure 7:
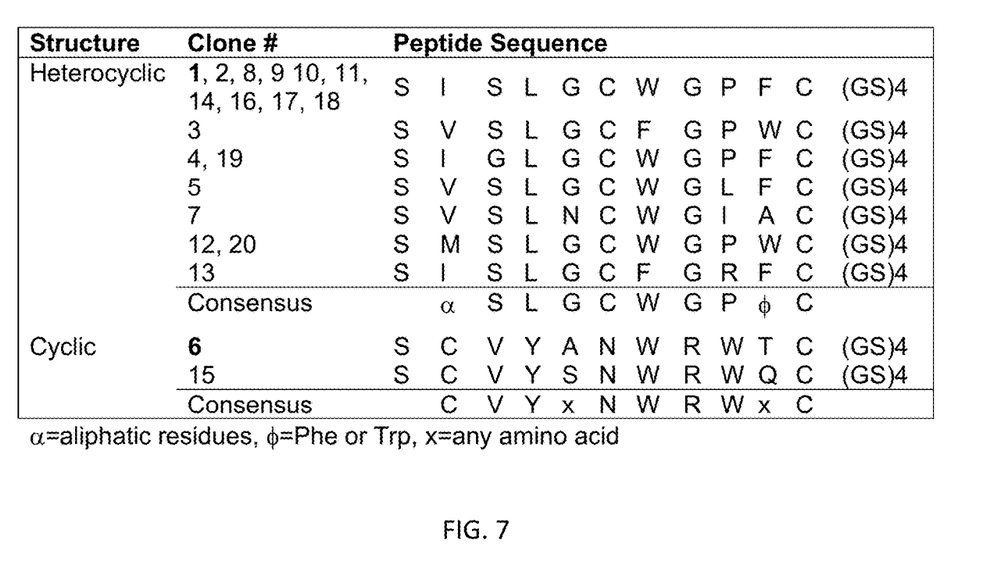
FIG. 7 illustrates Amino acid sequences of bladder cancer-specific binding peptides (BCSBPs).

In order to evaluate the specificity of Cyc6-functionalized MSN in vitro, binding was determined using fluorescent microscopy of whole cells and fluorimetric studies with extracted cell membrane proteins (FIG. 6). After 4 hours of binding, a clearly higher binding was observed on MB49 cells (FIG. 6A) than NIH3T$_3$ cells (FIG. 6B). This was confirmed quantitatively on extracted membrane proteins (FIG. 6C), where relative fluorescein intensities indicated fluorescent Cyc6-functionalized MSN bound to MB49 proteins at a significantly higher rate than to NIH3T$_3$ proteins (p<0.025). In addition, the Cyc6-functionalized membranes bound MB49 proteins at a higher rate than MSN without Cyc6, while the addition of freely floating MB49 membrane proteins further blocked binding.

Specificity of Cyc6 Peptide-Functionalized MSN in an Animal Bladder Cancer Model Measured by In Vivo MRI In order to measure specificity of Cyc6 on bladder tumors in vivo, mouse bladder tumors were established followed by exposure to MSN with or without Cyc6 peptide. MRI scans acquired immediately prior to particle instillation were used as non-labeled controls. Follow-up MRI scans were performed 24 hours after particle instillation to ensure the clearance of unbound particles by urination. MRI evaluation of the urinary volume confirmed clearance: normalized T1- and T2-weighted MRI values were return to control levels (T1: 398±33; T2: 664±64) and MSN-exposed (T1: 373±21; T2: 671±194) bladders. Both values are indicative of insignificant particle concentrations remaining in the urine.

The segmented tumor volumes were measured in MRI to be 7.4, 9.5, and 15.9 mm$^3$. The mouse with the 7.4 mm$^3$ tumor received the FITC-Gd$_2$O$_3$-MSN instillation, and the other 2 mice received the Cyc6-FITC-Gd$_2$O$_3$-MSN. Follow-up MRI scans were acquired 24 hours after instillation. MRI values were fat-normalized and plotted on the same color scale, with a clear hypointensity in the mice exposed to MSN functionalized with Cyc6. The average normalized value of the non-labeled tumors (582±88) was reduced by FITC-Gd$_2$O$_3$-MSN (540±118), and to a greater degree by Cyc6-FITC-Gd$_2$O$_3$-MSN (226±34; p<0.0001).

Identification of a Novel Bladder Cancer Cell Specific Peptide, Cyc6

Phage display is a method by which millions of different peptides can be screened at once against a target whose three dimensional structure is not known[30,70]. Degenerate peptides are expressed as fusions to the coat protein pIII of bacteriophage M13 after ligation of a degenerate double stranded oligonucleotide into a phage display vector. The phage library is then incubated with a target (i.e. a bladder cancer cell), washed extensively, eluted and, if needed, amplified. After several rounds of affinity purification, individual phage clones are plaque-purified and screened. The best phage clones can be further amplified in bacteria, isolated as double stranded DNA (replicative form), and subjected to DNA sequencing to determine the sequence of the expressed peptide.

Results from laboratory of Dr. John V. Frangioni were used. Dr. Frangioni has constructed a type 3 phage display vector with several properties that optimize expression of peptides as pIII fusions (vector mJ$_1$). Using mJ$_1$, three highly degenerate eight amino acid libraries in three different structures were constructed: 1) linear (L8 library), 2) cyclic via flanking cysteine residues that auto-oxidize in the bacterial periplasm (C8 library; ten amino acids total, including flanking cysteine residues), and 3) heterocyclic with four degenerate linear amino acids followed by four cysteine-cyclized amino acids (L4C4 library; ten amino acids total, including flanking cysteine residues, Table 1). Each peptide is 1,100 M.W. or less prior to addition of the (gly-ser) spacer. A length of eight degenerate positions was chosen to balance size minimization, diversity, helix formation (two and one half turns for linear peptides) and ring constraint (for cyclic and heterocyclic peptides). Sequencing of random clones from the libraries has confirmed the expected representation of all amino acids, except for a slight enrichment for tryptophan (data not shown). We routinely use an equi-complex mixture of all three libraries for screening since one or more structures may be preferentially selected by the target. Using living MB49 cells as the target for phage affinity purification, an equi-complex mixture of the three phage display libraries was purified for five rounds. There was a successive enrichment of phage binding to these cells, with saturation occurring after round 4 of affinity purification. Correlating with enrichment was a strong signal as assayed by indirect immunofluorescence.

Twenty individual phage clones were then plaque-purified and subjected to DNA sequence analysis. Of the 20 clones, 18 had an identical peptide sequence, or varied by only a single amino acid (Table 1). The remaining 2 clones differed from each other by only a single amino acid, but had a completely different sequence (and peptide structure) when compared to the other 18 peptides. Hence, two families of bladder cancer binding peptides were discovered. Two (heterocyclic clone number 1 and cyclic clone number 6) had nanomolar affinity for TCC cells. The actual per peptide affinity of these bladder cancer-derived peptides must await cloning of the as yet unknown cell surface target(s); however, based on comparisons to other phage/target model systems, actual affinity is likely in the 10-50 nM range. Indeed, phage binding to the surface of MB49 after 4 rounds of affinity purification cells is intense with only high picomolar to low nanomolar concentrations of applied phage. Most importantly, phage derived from MB49 bladder cancer cells appear quite specific for bladder cancer in general. These phage (and hence peptides) also bind to the unrelated mouse bladder cancer cell line MBT-2[71]. MB49 derived phage also bind equally well to six of six human bladder cancer cell lines tested, a resected low-grade human surgical specimen, and a canine bladder cancer cell line K9-TCC. Hence, the antigen recognized by these peptides is likely homologous in mouse, human and dog, is highly expressed on the cell surface, and may play an essential role in pathogenesis of the disease.

Cyc6 Functionalized MSN Show Enhanced Specificity for Bladder Cancer Cells and Extracted Membrane Proteins In Vitro.

Once identified, the 11 peptide sequence for Cyc6 was synthesized including a 4× repeat of (glycine-serine) onto the C-terminus. The FITC-Gd$_2$O$_3$-MSN particles were further functionalized with EDC/NHS molecules via a carbamic acid linker[60]. Binding to EDC/NHS occurs by way of a primary amine, though the exact amine by which the Cyc6 peptide binds to the MSN is unknown. The synthesized peptide has 3 primary amines: the N-terminus, the arginine residue, and the asparagine residue. The EDC/NHS technique allows for peptide binding by simple stirring. Thus, a pellet of FITC-Gd$_2$O$_3$-MSN was resuspended in a supernatant containing the Cyc6 peptide and mixed on a vortexer at low speed overnight at 4° C. After mixing, the particles were centrifuged at 16,000×g for 10 minutes, and 10 µL supernatant samples from before and after mixing were measured on a Nano-Drop 1000 UV-Vis spectrophotometer as described above.

Given sufficient time (up to 24 hours), we have observed near-total binding of non-specific FITC-Gd$_2$O$_3$-MSN on MB49 mouse TCC cells. However in clinical settings, there is a need for more rapid binding of bladder cancer cells and longer retention of bound particles (a "fast on, slow off" approach). In order to test the enhancement of rapid binding by Cyc6-FITC-Gd$_2$O$_3$-MSN to MB49 cells, binding was carried out for a maximum of 4 hours in tissue culture, at which point unbound particles were rinsed from the cells with phosphate buffered saline. Given a shorter window for binding, a high level of binding was observed under fluorescent microscopy for Cyc6-functionalized MSN on MB49 cells (FIG. 6A) compared with almost no binding for non-functionalized MSN. Thus we observe a higher affinity of our MSN for bladder cancer cells when functionalized with Cyc6.

The specificity was evaluated using an in vitro binding assay, in which extracted membrane proteins from MB49 cells were compared with those of $NIH3T_3$, a non-bladder cancer murine cell line. In preliminary experiments, the membrane protein concentration was varied between 0-7 mg/mL, and the MSN concentration was varied between 0-3 mg/mL. It was concluded that 7 mg/mL of membrane protein was sufficient to have a contiguous coat of protein on the surface of the well, preventing non-specific binding of MSN at 2 mg/mL to the plastic. The particles were allowed to bind for 90 minutes, at which point the plate was successively read and washed for 3 washes. Results (FIG. 6C) show demonstrably higher retention of all types of particles in MB49 cells relative to $NIH3T_3$ cells, which show an equivalent level of retention of fluorescence to an untreated (blank) well into which Cyc6-FITC-$Gd_2O_3$-MSN were added. The functionalized cyc6-FITC-$Gd_2O_3$-MSN show a statistically significantly higher binding to MB49 than to $NIH3T_3$ ($p<0.025$). It also showed a slightly increased binding to MB49 relative to non-functionalized FITC-$Gd_2O_3$-MSN, and in addition, the use of free MB49 membrane proteins as a blocking agent further reduced binding, though these differences were not statistically significant (p-values of 0.14 and 0.18, respectively).

Taken in total, the data indicate the Cyc6-FITC-$Gd_2O_3$-MSN do show improved specificity in vitro, both in terms of more rapid binding to MB49 cells relative to non-functionalized FITC-$Gd_2O_3$-MSN, and higher binding in MB49 cells relative to non-bladder cancer cells. By further characterizing the cell surface receptor this peptide is binding, we may be able to further enhance binding specificity as needed, resulting in additional improvements to in vivo bladder cancer labeling.

Cyc6-Functionalized MSN Show Enhanced Specificity for Bladder Tumors in a Mouse In Vivo Model.

In pre-clinical and clinical MRI, images are frequently acquired with $T_1$- or $T_2$-weighting, with $T_1$ referring to the spin-lattice, or flip angle, relaxation time, and $T_2$ referring to the spin-spin, or precessional relaxation time. Weighting is controlled by the MRI operator typically by varying the echo time ($T_E$) or relaxation time ($T_R$); $T_1$-weighted scans typically have a short $T_R$ and $T_E$, while $T_2$-weighted scans have a longer $T_R$ and $T_E$. A third imaging strategy using long $T_R$ and short $T_E$ minimizes $T_1$ and $T_2$ effects to generate an image based more on proton density[72]. On our Varian® 4.7 T small animal scanner, we have optimized scan parameters for proton density with slight $T_1$- and $T_2$-weighting; a typical $T_1$ weighted scan has a $T_R$ of 800 ms and a $T_E$ of 15 ms, while a typical $T_2$-weighted scan has a $T_R$ of 2300 ms and a $T_E$ of 15 ms. Using these parameters, the $T_2$-weighted scan typically provides better anatomical details, while both $T_1$- and $T_2$-weighted scans are enhanced by $Gd_2O_3$ contrast agents. These agents have moderate relaxivity values for both $R_1$ and $R_2$ and thus can provide contrast in $T_1$- and $T_2$-weighted MRI[22,73]. Thus, data presented herein emphasize $T_1$-weighting when more quantitative contrast is shown, and $T_2$-weighting when qualitative anatomic changes are shown. Study controls include no treatment (a negative control) as well as MSN without Cyc6. However, no gold standards used clinically can serve as a suitably comparable gold standard in our experimental paradigm. ImmunoCyt/uCyt™ and UroVysion™ are ex vivo tests which use monoclonal antibodies and in situ hybridization probes, respectively, on biopsied tissues[36,37] rather than an in vivo imaging approach. Hexvix, or hexyl aminolevulinate, is a dye containing porphyrins used in conjunction with fluorescent cystoscopy[38]. Cancer cells absorb the dye more readily than healthy epithelium and fluoresce pink. To date, we have not seen a report of cystoscopy-based approaches in murine models.

Unlike Conn., PET, and ultrasound, in which the image output is directly related to a physical property (density, positron emission, and acoustic impedance, respectively), the output of an MRI scan is unitless, with relative grayscale values related to the frequency response of the tissue to a particular pulse sequence. Thus, it is important to implement a consistent normalization strategy for comparison of tissues between different subjects and scans. To date, there is no agreed-upon methodology for normalizing MRI scans, though it is important that the normalization is consistent, replicable, and robust[74]. Thus, a normalization strategy was implemented that involves calculating the mean grayscale value of a region of fat, setting it to an arbitrary value such as 100 or 1000, and interpolating all values in the image between 0 and the arbitrary value. Fat is an ideal candidate for normalization because it is homogeneous, nearly always the brightest tissue in the scan, and with minimal vascularity, unlikely to be acutely affected by intravesicular injection of contrast agents.

Initially, 6 mice received intravesicular transplants of MB49 murine TCC cells. One week after implantation, 3 mice were determined by luciferase activity to have consistent tumor sizes and were justifiable for comparison. One other mouse had a very large tumor, and 2 others had almost no tumor. Immediately following the first set of IVIS scans, the 3 mice were taken to the small animal MRI; acquisitions include $T_1$-weighted axial scans, $T_2$-weighted axial scans, and $T_1$-weighted coronal scans. The mice were then given intravesicular instillation of 50 μL injections containing either FITC-$Gd_2O_3$-MSN or Cyc6-FITC-$Gd_2O_3$-MSN, and re-scanned the following day. With $T_1$-weighting, the borders of the tumors were difficult to identify, but appear as a slight lightening of the surrounding bladder space. The tumors are also slightly lighter than the bladder wall. With $T_2$-weighting, the tumor boundaries are much more distinct; the tumors show up as hypointense relative to the bladder space. Although the tumor boundaries were less clearly defined in the $T_1$-weighted MRI than the $T_2$ scans, the tumor volumes measured in each were consistent for all 3 mice, corroborating the IVIS findings.

The normalized $T_1$ intensities observed for the Cyc6-FITC-$Gd_2O_3$-MSN-exposed mice were higher than that of the FITC-$Gd_2O_3$-MSN-exposed mouse, while the $T_2$-weighted intensities for the Cyc6-FITC-$Gd_2O_3$-MSN-exposed mice were significantly more hypointense than that of the FITC-$Gd_2O_3$-MSN-exposed mouse. Taken together, this data indicates that the MSN containing Cyc6 have bound more effectively to the tumor than MSN alone. In this mouse model, the mice are typically sacrificed 2-3 weeks following the initial transplantation of the tumor. When the bladder is excised and sectioned, we observe fluorescence in the tumor, indicating strong retention of the particles. In addition, the mice were tested for a systemic immune response based on interferon-gamma (IFN-γ) production by splenocytes when stimulated with Cyc6. No IFN-γ production was detected. Because instillation was performed directly in the bladder, secondary organs (liver and kidneys) were not exposed to particles in this study. However, additional studies of intravenously injected MSN show no histopathological evidence of co-morbidity in exposed mice. Briefly, a number of cell lines were viable following doses up to 125 μg/mL in culture, and mice tolerated exposures up to 1 mg delivered intravenously (by tail vein or retro-orbital injection) without adverse changes in inflammatory cytokine production. In pregnant mice, we saw no evidence of adverse immune reaction or impact on growth in length or weight of the mothers or the embryos.

Example 3

Loading and Release Kinetics of Drug-Loaded Nanocarriers

Because of its high loading capacity and compatibility for functionalization, mesoporous silica has become a vehicle of interest for drug delivery systems (Yu-Shen Lin, 2001). Nanoparticle-based drug delivery systems consist of two main components: the ability to target desired cells with the particles, and the ability to load and release a payload at the desired location. Both components have the potential to reduce the necessary quantity of payload required and reduce negative side effects of the payload (Yu-Shen Lin, 2001).

There has been some success accelerating payload release through the use of ultrasound (Juan L. Paris, 2015). The ability to limit payload release until exposure to ultrasound would allow researchers to use the same delivery method for any target that can be exposed to ultrasound. In our experiments involving the use of ultrasound to accelerate diffusion, it was apparent that whether the ultrasound was used or not, given a certain time allotment, the contents in the particles still dispersed. We must devise a method to delay passive diffusion until the particles arrive at the desired location and ultrasound can be used to accelerate release. To prevent this unwanted dispersion, the particles were capped with gelatin and then cross-linked with glutaraldehyde[75]. The use of this gelatin capping method has resulted in delay in payload release. Fluorescein takes approximately 3 hours to diffuse from gelatin capped particles without the use of ultrasound. Time required for fluorescein depletion is decreased with the use of ultrasound. As a prototype for intravesical drug delivery in TCC, this example focuses on the release of mytomycin c from gelatin capped MSN.

MSN are first loaded with a bioactive agent by diffusion. In this example, small interference RNA (siRNA) targeting VEGF expression by TCC cells was used as a prototype. Ten mg of MSN material were added to 2 mg siRNA in 1 mL diluent (DMSO) and vortexed at 4° C. for 24 h. This suspension is centrifuged for 30 min at 16,000×g. The supernatant is retained to spectroscopically determine the quantity of bioactive agent loaded in the particles. Typically 200 μg agent is loaded in 1 mg of MSN material. The bioactive-loaded MSN material is resuspended in 1 mL of 1 wt. % low melting point gelatin and shaken on a vortexer at 40° C. for 2 h. Fifteen microliters of 50% glutaraldehyde was added to crosslink the gelatin, and vortexing continued for 30 min at 40° C. The excess gelatin was washed by centrifugation for 30 min at 16,000×g and resuspending the pellet in 1 mL deionized water. A final round of centrifugation for 30 min at 16,000×g was completed, the supernatant discarded, and the particles were frozen in liquid nitrogen and vacuum dried overnight. Once dried, the particles were stored at 4° C. until used.

The experiment was carried out using a UV-Vis spectrophotometer by recording optical density over time. To start, 1 mg of loaded particles was resuspended in 100 microliters of 1×PBS. This was added to the bottom of a quartz cuvette. The particles were centrifuged at 80×g for 3 minutes to form a loose pellet, and 600 μL of 1×PBS was gently added to the cuvette. In other experiments, the diluent was changed to an artificial urine analog to mimic the intravesical chemical environment. As the agent disperses from the particles, readings are taken of the surrounding fluid above the nanoparticles. For siRNA, absorbance at 260 nm was measured every 5 minutes for 18 hours.

In another embodiment, MSN are loaded with a hydrophobic molecule by osmotic pressure. In this case, cannabidiol (CBD) is a molecule of great interest in bladder cancer for its ability to modulate detrusor muscle activity and for its antiproliferative properties. While MSN are first washed with methanol, CBD is first prepared in a stock solution of 30 mg/mL methanol, then added to 20 vol. % $H_2O$. When the hydrophobic CBD is added to the particles and stirred for 24 h, osmotic pressure forces it into the MSN pores. To further increase CBD loading, this process is repeated for multiple stirring stages. Over a series of trials, an average of 1.1 mg CBD was loaded per mg of MSN. To measure release of CBD from the MSN, a sample of MSN in 1 mL $H_2O$ was placed in dialysis tubing immersed in 35 mL diluent (methanol or phosphate buffered saline), with 1 mL samples of diluent collected at set time points. The samples were concentrated by evaporation and the CBD quantified spectroscopically.

Figure 8A:
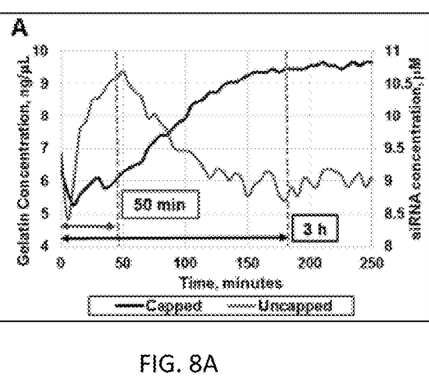
FIG. 8A-B illustrate controlled release of payload from capped nanocarriers.
Figure 8B:
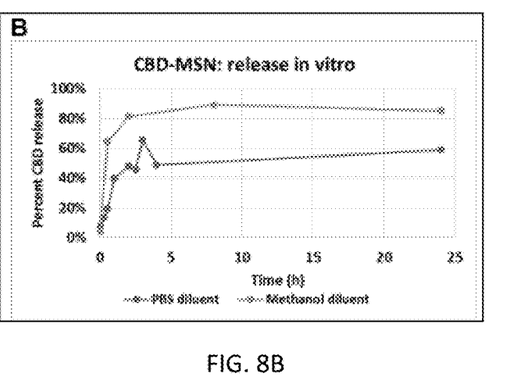

Typical results for this experiment type are shown (FIG. 8A). In cases where the particles are not capped, the hydrophilic bioactive agent is measured directly in the spectrophotometer. For instance, the siRNA concentration is measured by absorbance at 260 nm (red curve) and maximum release occurs in 50 min. When gelatin is used as a capping agent, the UV-Vis spectrum of the bioactive agent may be overwhelmed by the gelatin spectrum, in which case the absorbance at 230 nm arising from dispersion of gelatin is used. In this example, the release of siRNA was delayed to 3 h (black curve). Similar results were obtained with other hydrophilic bioactive agents including anti-tumor drugs such as epirubicin, mitomycin-c, gemcitabine, and docetaxel. The degree of delayed release can be modified by changing the composition of gelatin and/or glutaraldehyde cross-linking. In the case of hydrophobic CBD (FIG. 8B), the release was complete within 3 h when using methanol as a diluent (orange curve). In phosphate buffered saline (blue curve), 50% of CBD was released in 2 h, with maximal release occurring over 4 h.

The invention claimed is:

1. A composition for bladder tumor monitoring and for controlled delivery of bioactive materials comprising: mesoporous silica nanoparticles (MSNs), said MSNs being covalently functionalized with at least one material selected from the group consisting of a lanthanide, a fluorophore and, an agent detectable by ultrasound, whereby the MSNs are capped with gelatin or a synthetic phospholipid bilayer, and further providing that the material is covalently linked with a bladder cancer cell specific Cyc6 peptide.

2. The composition of claim 1 wherein the agent comprises trifluoropropyl groups.

3. The composition of claim 1 whereby the MSNs further comprise a substance selected from the group consisting of gold, bismuth, and iron oxide.

4. The composition of claim 1 that is $Cyc_6$-FITC-$Gd_2O_3$-MSN.

5. A composition for delivering a therapeutic composition to bladder cancer cells in a mammal comprising: mesoporous silica nanoparticles (MSNs), said MSNs being loaded with one or more bioactive agents, said MSNs further being covalently linked with a bladder cancer cell specific Cyc6 peptide, whereby the MSNs are capped with gelatin or a synthetic phospholipid bilayer, said gelatin or synthetic phospholipid bilayer being crosslinked with glutaraldehyde.

6. The composition of claim 5 whereby the bioactive agent is an antimitotic agent or an immunogenic substance.

7. The composition of claim 5 whereby the bioactive agent is selected from the group consisting of cannabidiol, epirubicin, mitomycin-c, gemcitabine, and docetaxel.

8. The composition of claim 5 whereby the MSNs are capped with gelatin having a melting point of between about 35-45° C.

9. The composition of claim 5 whereby the MSNs are capped with a synthetic phospholipid bilayer comprising one or more types of fatty acids and cholesterol.

10. A method for sequential imaging and/or imaging diagnostic or therapeutic cells in a mammal, comprising:
    a) introducing to a mammal a composition comprising mesoporous silica nanoparticles (MSNs), said MSNs being covalently functionalized with at least one material selected from the group consisting of a lanthanide, a fluorophore and, an agent detectable by ultrasound, whereby the MSNs are capped with gelatin or a synthetic phospholipid bilayer; and further providing that the MSNs are covalently linked with a bladder cancer cell specific Cyc6 peptide (Cyc6); and
    b) detecting the composition in the mammal.

11. The method of claim 10 wherein the MSNs are less than about 200 nm in diameter.

12. The method of claim 10 wherein the composition is injected into the mammal by a route selected from the group consisting of subcutaneously, intradermally and intravascularly.

13. A method for delivering a therapeutic composition to bladder cancer cells in a mammal comprising:
    a) loading mesoporous silica nanoparticles (MSNs) with a bioactive agent to form bioactive-loaded MSNs, said MSNs being covalently linked with a bladder cancer cell specific Cyc6 peptide (Cyc6);
    b) capping the bioactive-loaded MSNs with gelatin or a synthetic phospholipid bilayer to form capped MSNs; and
    d) administering the capped MSNs to the mammal.

14. The method of claim 13 whereby the bioactive-loaded MSNs are capped with low melting point gelatin.

15. The method of claim 13 whereby the gelatin or synthetic phospholipid bilayer is cross-linked with glutaraldehyde.

* * * * *